(12) United States Patent
Hebenstreit et al.

(10) Patent No.: US 12,167,977 B2
(45) Date of Patent: Dec. 17, 2024

(54) LIMB ORTHOSIS, IN PARTICULAR KNEE BRACE

(71) Applicant: Bauerfeind AG, Zeulenroda-Triebes (DE)

(72) Inventors: Sandro Hebenstreit, Zeulenroda-Triebes (DE); Gerald Stier, Langenwetzendorf (DE); Hans B. Bauerfeind, Zeulenroda-Triebes (DE)

(73) Assignee: Bauerfeind AG, Zeulenroda-Triebes (DE)

(*) Notice: Subject to any disclaimer, the term of this patent is extended or adjusted under 35 U.S.C. 154(b) by 69 days.

(21) Appl. No.: 16/766,586

(22) PCT Filed: Nov. 23, 2018

(86) PCT No.: PCT/EP2018/082346
§ 371 (c)(1),
(2) Date: May 22, 2020

(87) PCT Pub. No.: WO2019/101910
PCT Pub. Date: May 31, 2019

(65) Prior Publication Data
US 2021/0022900 A1    Jan. 28, 2021

(30) Foreign Application Priority Data

Nov. 23, 2017  (DE) .......................... 102017220968.2

(51) Int. Cl.
*A61F 5/01*  (2006.01)
(52) U.S. Cl.
CPC .......... *A61F 5/0109* (2013.01); *A61F 5/0123* (2013.01); *A61F 5/013* (2013.01);
(Continued)

(58) Field of Classification Search
CPC ...... A61F 5/0109; A61F 5/0123; A61F 5/013; A61F 5/0125; A61F 5/32; A61F 5/01;
(Continued)

(56) References Cited

U.S. PATENT DOCUMENTS 5,599,288 A     2/1997  Shirley et al.
2009/0182254 A1*  7/2009  Cho ...................... A61F 5/0123
                                                             602/26
(Continued)

FOREIGN PATENT DOCUMENTS

DE    102010054579    6/2012
DE    102015100628    7/2015
(Continued)

OTHER PUBLICATIONS

International Search Report and Written Opinion for PCT/ EP2018/ 082346 dated Mar. 4, 2019, 11 pages, with English translation of ISR.

(Continued)

*Primary Examiner* — Victoria Hicks Fisher
*Assistant Examiner* — Daniel A Miller
(74) *Attorney, Agent, or Firm* — Sheppard Mullin Richter & Hampton LLP

(57) ABSTRACT

The present invention relates to a limb orthosis, in particular a knee orthosis, comprising a strap system, wherein a strap as a first section of the strap system is routed in such a manner that the strap crosses over in a first crossover region and that a strap as a second section of the strap system is routed in such a manner that the strap crosses over in a second crossover region.

14 Claims, 14 Drawing Sheets

Figure 1:
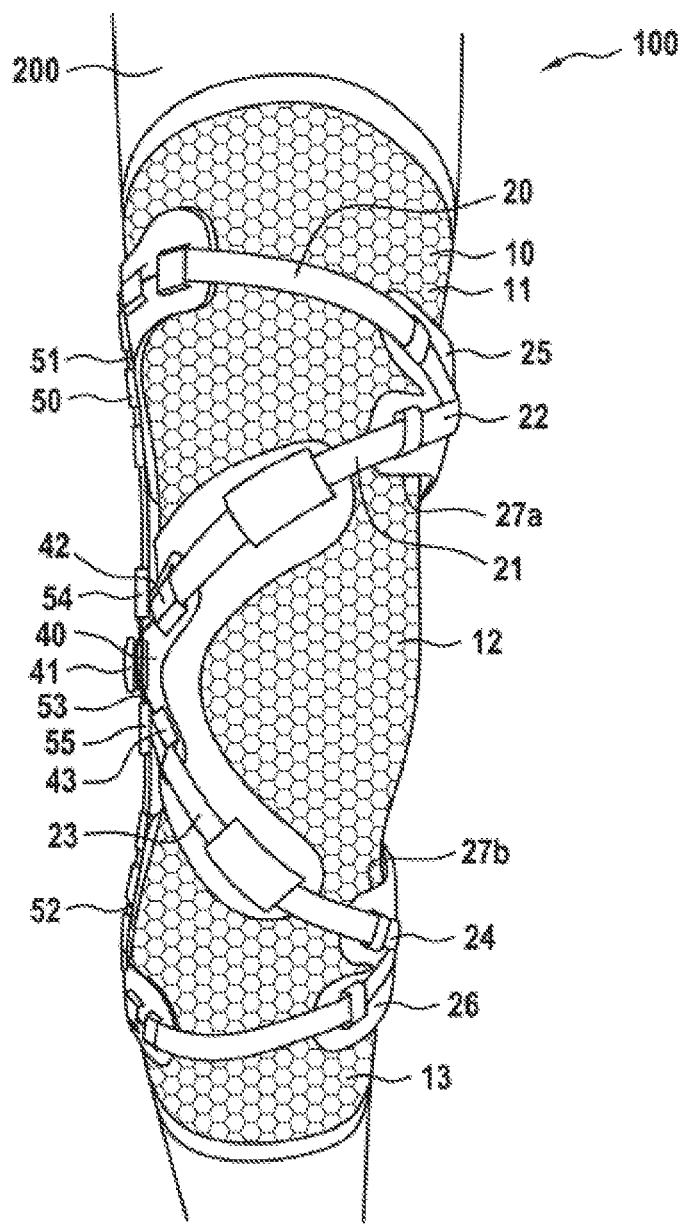

(52) U.S. Cl.
CPC ................ *A61F 2005/0137* (2013.01); *A61F 2005/0144* (2013.01); *A61F 2005/0179* (2013.01)

(58) Field of Classification Search
CPC .. A61F 5/26; A61F 5/30; A61F 5/0106; A61F 5/0102; A61F 2005/0137; A61F 2005/0144; A61F 2005/0179; A61F 2005/0197; A61F 2005/0151; A61F 2005/0172; A61F 2005/0148; A61F 2005/0165; A61F 2005/0139; A61F 2005/0176; A61F 2005/0167; A61F 2005/0124; A61F 2005/0181; A61F 5/00; A61F 5/0111; A61F 5/3723; A61F 5/37; A61F 5/05841; A61F 5/0585; A61F 5/05858; A61F 5/0118; A61F 5/10; A61F 5/373; A61F 2005/0141; A61F 2005/0174; A61F 2005/0188; A61F 2005/0132; A61B 5/70
USPC ........................................ 602/16, 20, 23, 26
See application file for complete search history.

(56) References Cited

U.S. PATENT DOCUMENTS

| | | | | |
|---|---|---|---|---|
| 2011/0004135 A1* | 1/2011 | Kausek | ................ | A61F 5/0123 602/16 |
| 2011/0137220 A1 | 6/2011 | Vollbrecht et al. | | |
| 2011/0201983 A1* | 8/2011 | Swanson | ............... | A61F 5/0125 602/16 |
| 2013/0296757 A1 | 11/2013 | Kaphingst | | |
| 2014/0214016 A1* | 7/2014 | Ingimundarson | ..... | A61F 5/0123 606/16 |
| 2015/0305909 A1* | 10/2015 | Kausek | ............... | A61F 5/0109 602/16 |
| 2015/0305910 A1 | 10/2015 | Swanson | | |
| 2016/0095734 A1* | 4/2016 | Sigurdsson | ........... | A61F 5/0102 602/26 |
| 2016/0367391 A1* | 12/2016 | Paulos | .................. | A61F 5/0106 |
| 2019/0159921 A1* | 5/2019 | Pattke | .................. | A61F 5/0118 |
| 2022/0015938 A1* | 1/2022 | Soifer | .................. | A61F 5/0123 |

FOREIGN PATENT DOCUMENTS

| | | | | |
|---|---|---|---|---|
| DE | 102015100628 A1 * | 7/2015 | ........... | A61F 5/0109 |
| JP | 2003523235 A | 8/2003 | | |
| WO | 2001056498 A2 | 8/2001 | | |
| WO | WO-2014/043695 | 3/2014 | | |
| WO | 2014006917 A1 | 9/2014 | | |

OTHER PUBLICATIONS

International Preliminary Report on Patentability for PCT/EP2018/082346 dated Nov. 19, 2019, 5 pages.

Search Report for RU Application 2020120540/14(035015) dated Apr. 9, 2021, 2 pages.

* cited by examiner

LIMB ORTHOSIS, IN PARTICULAR KNEE BRACE

CROSS-REFERENCE TO RELATED APPLICATIONS

This application is a U.S. National Stage Application under 35 U.S.C. §371 of International Application No. PCT/EP2018/082346, filed Nov. 23, 2018, which claims priority to DE 102017220968.2, filed Nov. 23, 2017, the contents of which are incorporated to the present disclosure by reference.

The present invention relates to an orthosis for limbs, in particular a knee orthosis or an elbow orthosis, comprising a strap system preferably coupled by means of a coupling element, characterized in that a strap as a first section of the strap system is routed in such a manner that the strap crosses over in a first crossover region and that a strap as a second section of the strap system is routed in such a manner that the strap crosses over in a second crossover region.

The present invention relates in particular to an orthosis for limbs, in particular a knee orthosis or an elbow orthosis, comprising a carrier element having an upper subregion, a middle subregion and a lower subregion and comprising a strap system coupled to the carrier element by means of a coupling element, wherein a strap as a first section of the strap system is routed around the upper subregion of the carrier element in such a manner that the strap crosses over in a first crossover region and that a strap as a second section of the strap system is routed around the lower subregion of the carrier element in such a manner that the strap crosses over in a second crossover region. The invention also relates to the use of the limb orthosis according to the invention, particularly a knee orthosis or an elbow orthosis for treating knee disorders or elbow disorders and methods for treating knee disorders or elbow disorders by means of the limb orthosis according to the invention.

Orthoses for limbs, also referred to as limb orthoses, particularly knee orthoses for the passive and active stabilization of the knee joint, are known from prior art. Such knee orthoses frequently have a carrier element in the form of a support, on which stabilization elements such as straps, rods or joint splints are mounted, as is shown in DE 200 05 366 U1.

Such knee orthoses are used for example for a knee arthrosis or after injuring the interior meniscus to take strain off the affected region and to stabilize it.

Knee orthoses thereby frequently have straps with which the knee orthosis is adjusted, in other words to the shape of the leg and/or the range of action. Specifically, routed straps are known for example from EP 2 612 626 A2, DE 40 136 93 A1 and DE 198 44 545 A1.

The technical problem of the present invention is to provide an improved orthosis for limbs, particularly knee orthoses. In particular, the limb orthosis, particularly knee orthosis, is to be especially well suited for treating medial gonarthrosis and thereby take strain off the medial or inner compartment of the femorotibial joint and thus lead to improved pain relief. The knee orthosis is thereby also meant to fit firmly and securely on the leg.

The present invention solves the technical problem by means of an orthosis for a limb, in particular a knee orthosis according to claim 1.

In the present invention, a limb refers in particular to a leg or an arm, wherein the hip region may be included as part of a limb. However, in connection with the present invention, in addition especially to leg orthoses, knee orthoses, arm orthoses or elbow orthoses, an orthosis for limbs also refers to a hip orthosis. Preferably the limb orthosis is a knee orthosis, elbow orthosis or hip orthosis.

The orthosis for limbs, also referred to as a limb orthosis, may also involve in particular a knee orthosis or an elbow orthosis. It preferably involves a knee orthosis.

The present invention relates to an orthosis for limbs, particularly a knee orthosis, comprising a strap system, characterized in that a strap as a first section of the strap system is routed in such a manner that the strap crosses over in a first crossover region and that a strap as a second section of the strap system is routed in such a manner that the strap crosses over in a second crossover region.

The present invention relates in particular to a limb orthosis, comprising a strap system characterized in that a strap as a first section of the strap system is routed in such a manner that the strap crosses over in a first crossover region and that a strap as a second section of the strap system is routed in such a manner that the strap crosses over in a second crossover region, and comprising a coupling element to which the first section of the strap system and the second section of the strap system are coupled, wherein for the donned limb orthosis the first section and the second section of the strap system are routed around the limb in such a manner that the first section and the second section of the strap system wrap around the limb and thereby cross over at least once. When the first section and/or the second section of the strap system wrap around the limb, in other words routed at least once entirely around the limb, preferably both ends of the first section and/or the second section are connected to the coupling element.

For a knee orthosis in a donned state, the first section of the strap system contacts the upper thigh; the second section of the strap system in the donned state contacts the lower thigh.

For a knee orthosis in the donned state, the first section of the strap system preferably wraps around the upper thigh; the second section of the strap system in the donned state wraps around the lower thigh. For an elbow orthosis, the first section of the strap system in the donned state contacts the upper arm; the second section of the strap system in the donned state contacts the lower arm.

For an elbow orthosis in the donned state, the first section of the strap system preferably wraps around the upper arm; the second section of the strap system in the donned state preferably wraps around the lower arm.

Preferably the limb orthosis, preferably knee orthosis, comprises a coupling element to which are coupled the first section of the strap system and the second section of the strap system. Preferably, in the donned state the coupling element contacts the leg at the level of the knee. Preferably, when the knee orthosis is donned, the coupling element is positioned on the outside of the leg.

When the orthosis according to the invention is donned, the coupling element may be positioned on the outside or the inside of the limb, as needed. For example, when used on a "bow leg," the coupling element may be positioned on the outside of the leg, and when used on a "knock-knee," the coupling element can be positioned on the inside of the leg.

Thus, the strap system forms two crossover regions, of which one lies above the knee and the other below the knee. Surprisingly, it was shown that these two crossover regions advantageously result in the knee orthosis fitting in a positionally stable manner on the upper thigh as well as the lower thigh. Such a positional stability is a key prerequisite for the constantly high effectiveness of the knee orthosis. In addition, the two crossover regions may preferably serve in an advantageous manner as a counter-support for the vertex force on the outside of the knee. Advantageously, the two crossover regions allow one to also omit a spacer on the inside of the knee orthosis if the crossover regions in a preferred embodiment come to rest on the inside of the leg and the coupling element in a preferred embodiment is positioned at knee-level in such a manner that it comes to rest on the outside of the leg. Preferably, when the knee orthosis is donned, the two crossover regions are positioned on the inside of the leg.

Advantageously, the orthosis according to the invention can be used for correcting misaligned joints, for example "bow legs" or "knock knees." The orthosis according to the invention can also be used advantageously to limit joint flexion or joint extension.

It was shown that the structure according to the invention of the knee orthosis results in the knee orthosis being more comfortable to wear, wherein it takes a load off the knee at least as well as knee orthoses from prior art. The knee orthosis according to the invention is thereby less rigid than those from prior art.

For an elbow orthosis, it comprises correspondingly a coupling element to which are coupled the first section of the strap system and the second section of the strap system. Preferably, in the donned state the coupling element contacts the arm at elbow-level. Preferably, when the elbow orthosis is worn the coupling element is positioned on the outside of the arm.

Preferably for limb orthoses, in particular knee orthoses, the first strap section and/or the second strap section are routed as a crossing sling around the leg or arm. Preferably for limb orthoses, in particular knee orthoses, the first strap section and the second strap section are each routed as a crossing sling around the leg or arm.

The preferred routing, according to the invention, of the strap sections in a sling form can significantly assist the effect of the strap system.

Thus, preferably the first section and/or the second section of the strap system is routed around a limb, in particular a leg, in such a manner that the strap section wraps around the limb and thereby crosses over itself at least once, preferably once. Preferably, the ends of the first section and/or the second section of the strap system are thereby attached to the coupling element, particularly in the central region of the limb orthosis, in particular the knee orthosis.

Thus, a limb orthosis is preferred, wherein when the limb orthosis is donned, the first section and/or the second section of the strap system are routed around the limb, particularly a leg, in such a manner that the first section and/or the second section of the strap system wraps around the limb and thereby crosses over itself, in other words wherein the first section and/or the second section of the strap system are each routed in a figure-eight form around the limb.

Regarding the orthosis for limbs, in particular a knee orthosis, there may also be a carrier element, for example a support; however, the pathway of the strap system according to the invention may allow one to also omit the carrier element.

Thus, the present invention also relates to an orthosis for limbs, in particular a knee orthosis, comprising a carrier element having an upper subregion, a central subregion and a lower subregion, and comprising a strap system coupled to the carrier element via a coupling element, characterized in that a strap as the first section of the strap system is routed around the upper subregion of the carrier element in such a manner that the strap crosses over in a first crossover region and that a strap as a second section of the strap system is routed around the lower subregion of the carrier element in such a manner that the strap crosses over in a second crossover region.

In the donned state, the upper subregion of the carrier element contacts the upper thigh or upper arm; in the donned state, the lower subregion of the carrier element contacts the lower thigh or lower arm, and in the donned state, the central subregion of the carrier element contacts the leg in the region of the knee or the arm in the region of the elbow.

Thus, the limb orthosis, in particular knee orthosis, has a strap system, which is routed around the leg or the arm of the wearer, in other words preferably also around the carrier element, in a double figure-eight form, wherein particularly the first upper eight is routed on the upper subregion of the carrier element, which in the donned state contacts the upper thigh or upper arm, and the second lower eight is routed around the lower second subregion of the carrier element, which in the donned state contacts the lower thigh or lower arm.

The straps of the strap system can preferably be routed on the carrier element, in the carrier element or under the carrier element. One can also omit a carrier element.

In a preferred embodiment, the coupling element is attached to the central subregion on the carrier element. Preferably, the coupling element is attached to the central subregion on the carrier element in such a manner that when the limb orthosis is donned, it is positioned on the outside of the leg or arm. Preferably the coupling element is attached to the central subregion on the carrier element in such a manner that when the knee orthosis is donned, it is positioned on the outside of the leg.

Preferably, the two crossover regions are attached to the carrier element in such a manner that when the limb orthosis is donned, they are positioned on the inside of the limb.

Preferably, the two crossover regions are attached on the carrier element in such a manner that when the knee orthosis is donned, they are positioned on the inside of the leg.

In a preferred embodiment, the carrier element is a support. Suitable supports are known to a person skilled in the art. In particular, a carrier element may be a support in the form of knitwear, for example a knitted fabric or a crocheted fabric. Preferably, the support is a textile support.

In a preferred embodiment, the strap system has a first crossing element into which the strap is routed in a first crossover region and it has a second crossing element into which the strap is routed in a second crossover region. The crossing elements may advantageously serve as guideways for the straps.

Preferably, the first crossing element can be attached reversibly to the upper subregion of the carrier element and the second crossing element can be attached reversibly to the lower subregion of the carrier element.

The crossing elements may advantageously serve as guideways for the straps in order to also affix the crossover region reversibly on the carrier element. This advantageously allows an exact and yet flexible positioning of the two crossover regions so that these fit in a particularly good positionally stable manner and can act precisely.

In a preferred embodiment, the first and the second crossing elements are reversibly attachable by means of a hook and loop connection to various locations of the carrier element.

By means of a hook and loop connection, the crossing elements can be reversibly attached in a simple and secure manner. For example, the carrier element may have loop or hook regions on which a crossing element can be positioned and attached. The crossing element thereby preferably has on its bottom side a hook or loop surface. With a corresponding loop or hook region on the carrier element, a surface can advantageously be provided in which the crossing element can be freely positioned, and simultaneously for the sake of effectiveness, the positioning, dimensions and shape of the hook or loop region on the carrier element, can define sensible regions on which the crossing elements should be attached.

In a preferred embodiment, the first section of the strap system is formed by a first strap and the second section of the strap system is formed by a second strap. Thus, in this preferred embodiment, the first upper figure-eight is formed by a first strap and the second lower figure-eight is formed by a second strap. Preferably, both straps are thereby attached to the coupling element.

In a preferred embodiment, the strap system is movably attached to the coupling element. The movable attachment may be for example in the form of a rotatable suspension of the straps on the coupling element. In the region of the coupling element, the straps can thereby also change their routing on the leg, arm or carrier element if the positioning of the crossover regions is changed.

The straps of the strap system may consist either of flat belts, in particular essentially inelastic flat belts, or cables or cords, which run preferably in tunnels, which are formed of flat strips for example. This has the advantage that the straps do not create folds when tensioning or loosening.

In a preferred embodiment, the coupling element has a tension element for tensioning the strap of the first section of the strap system and/or for tensioning the strap of the second section of the strap system. Advantageously, it is also provided that the two straps can be tensioned together or separately so that on the one hand they allow a tight fit of the limb orthosis to the limb, in particular the knee orthosis to the leg, and on the other, they allow good positioning and a good fit of a preferred joint splint.

In a preferred embodiment, the tensioning element is constructed as a rotary knob with which both straps can be tensioned simultaneously. Thus, preferably the straps are tensioned by rotating a knob, for example by the rotary knob winding up cords that are connected to the straps or the straps are designed as cords that are wound up using the rotary knob. Thus, it is preferably provided that the two straps are tensioned simultaneously by a tensioning element so that the two straps have the correspondingly same tension force and thus the two straps as a strap system are combined into one single tension system and only one task step is necessary for tensioning both straps. Preferably the tensioning system is attached to the coupling element or like the coupling element itself to the central subregion on the carrier element. Naturally, the tensioning element is designed in such a manner that the straps can also be loosened again. For example, by means of increments in the rotary knob, one can preferably set various tension levels so that a specific force setting is advantageously possible.

Thus, the invention is characterized in particular by routing the straps as a double figure-eight, wherein the straps are tensioned against each other by means of a central tensioning element and are routed symmetrically via double strap crossovers to the upper and lower end of the orthosis, where they each form a sling. Preferred advantages are thereby in particular a symmetrical tension input and one single tensioning system for tensioning the straps over the entire orthosis. The system can also be used with or without a carrier element.

By means of the specific, symmetrical strap routing with a self-contained sling formation, a position correction of the upper thigh or upper arm in relation to the lower thigh or lower arm is achieved.

In a preferred embodiment, the limb orthosis, in particular a knee orthosis, also has a joint splint.

Joint splints are usually designed in such a manner that the knee motion can take place not only in the sagittal element but that an adjustment can also take place in the frontal plane. In the frontal plane, there are adjustable hinge joints that are located as close as possible to the bend apex of the knee joint or elbow joint to thereby act within the meaning of load-relief of the inner compartment of the femorotibial joint or elbow joint. The circularly arranged straps shown in prior art act as counter-supports above and below the knee joint on the opposite side of the joint splint. Such joint splints are known for example from WO 2007/145504 A1 or WO 2003/103547 A1.

Surprisingly, it was shown that by the double-crossed routing of the strap system according to the invention, the joint splint, and preferably the carrier element, is pressed particularly well against the leg or the arm, in particular on the outside of the leg or arm, in a positionally stable manner, since the two preferably interior crossover regions act as counterforces to the coupling element, which is preferably attached to the joint splint. In this way, in a preferred embodiment the limb orthosis, in particular knee orthosis, can act particularly well biomechanically according to the three-force principle (two main attachment points and one oppositely acting pressure point). Such an action based on the three-force principle is advantageously suited to support the repositioning of upper and lower thigh bones or upper and lower arm bones via the joint itself. One can thereby preferably correct the joint space counter to the clinical condition and significant pain relief can thereby result.

Preferably, the joint splint is attached to the limb orthosis, in particular knee orthosis, in such a manner that when the orthosis is worn, it is positioned on the outside of the leg or arm. However, if necessary, the joint splint can also be positioned on the inside of the leg or arm.

Preferably, the joint splint is attached on the carrier element in such a manner that when the limb orthosis, in particular knee orthosis, is worn, said splint is positioned on the outside of the leg or arm.

In a preferred embodiment, the joint splint has a first bar section, a second bar section and a third bar section, wherein the first bar section and the second bar section are each connected by a hinge to the third bar section.

In a preferred embodiment, the joint splint has a first bar section in the region of the upper subregion of the carrier element, a second bar section in the region of the lower subregion of the carrier element, and a third bar section in the region of the central subregion of the carrier element, wherein the first bar section and the second bar section are each connected by a hinge to the third bar section.

Preferably, the coupling element and thus preferably also the tensioning element are attached to the third bar section in the region of the central subregion of the limb orthosis, in particular knee orthosis, preferably of the carrier element on the joint splint. In particular, the central bar section can also form the coupling element.

In a preferred embodiment, the bar sections are designed to be elastic.

In a preferred embodiment, the third bar section is formed of a spring element, in particular a leaf spring.

In a preferred embodiment, the hinges are monocentric hinges. The two monocentric hinges above and below the third central bar section jointly result in a duo-centric configuration, which advantageously results in a bending of the knee causing less stress in the knee joint. While bending, the center of rotation can repeatedly change from one center of rotation to another. Combined with elastic bars, in particular the leaf spring, the duo-centric configuration ensures that the orthosis does not shift laterally against the limb axis, in particular leg axis, when bending.

The design of the third bar section out of a spring element, in particular out of a leaf spring, for example spring steel, results in that the first bar section and the second bar section not only rotate in one axis, but are also movable in an axis rotated by 90°, and specifically preferably in the region in which, by means of the coupling element, the central force application point of the three-point system created by the strap system is flexible. In addition, the two hinges, which connect the first bar section and the second bar section, respectively, to the third bar section result in the joint splint as such being much better adjustable to the contours of the body. Also, the flexibility of the third bar section advantageously results in the limb orthosis, in particular knee orthosis, being able to yield somewhat during extreme motions and thereby warns the user of an excessively incorrect leg movement.

Through the design of the third bar section as a spring element, the central force application point is advantageously spring-mounted.

The design of the strap system, in other words the figure-eight routing, is designed in such a manner that the strap crossings cannot migrate to the center of the knee or the center of the elbow. The lateral bar thereby serves as a spacer for the two medial strap crossings. In this way, optimal positional stability of all function elements to each other is assured. In addition, the orthosis thereby remains positionally stable on the leg or arm.

The present invention also relates to the use of an orthosis according to the invention for treating limb pain.

The present invention also relates to the use of a knee orthosis according to the invention for treating knee pain, in particular knee joint arthrosis, also referred to as gonarthrosis. Gonarthrosis refers to wear of the cartilaginous joint surface of the knee joint. When the medial or inner compartment of the femorotibial joint is affected, this is referred to as a medial gonarthrosis. Varus gonarthrosis is present if the patient suffers from bow legs at the same time. If the lateral or outer compartment of the femorotibial joint is affected, this is referred to as a lateral gonarthrosis. Valgus gonarthrosis is present if the patient is knock-kneed at the same time. Preferably, the knee orthosis according to the invention is used for a medial gonarthrosis, in particular for relieving pressure on the inner compartment of the femorotibial joint and reducing pain.

The present invention also relates to a treatment method for treating gonarthroses, in particular medial gonarthroses, in which a knee orthosis according to the invention is applied to the leg of a patient in such a manner that the two crossover regions on the inside of the leg contact the leg and the coupling element on the outside of the leg contacts the leg.

The present invention also relates to a treatment method for treating limb pain, in which a limb orthosis according to the invention is applied to the limb of a patient in such a manner that the two crossover regions on the inside of the limb contact the limb and the coupling element on the outside of the limb contacts the limb.

The invention is further explained by means of an example and the drawings, wherein these are not to be understood as restrictive.

Figure 2A:
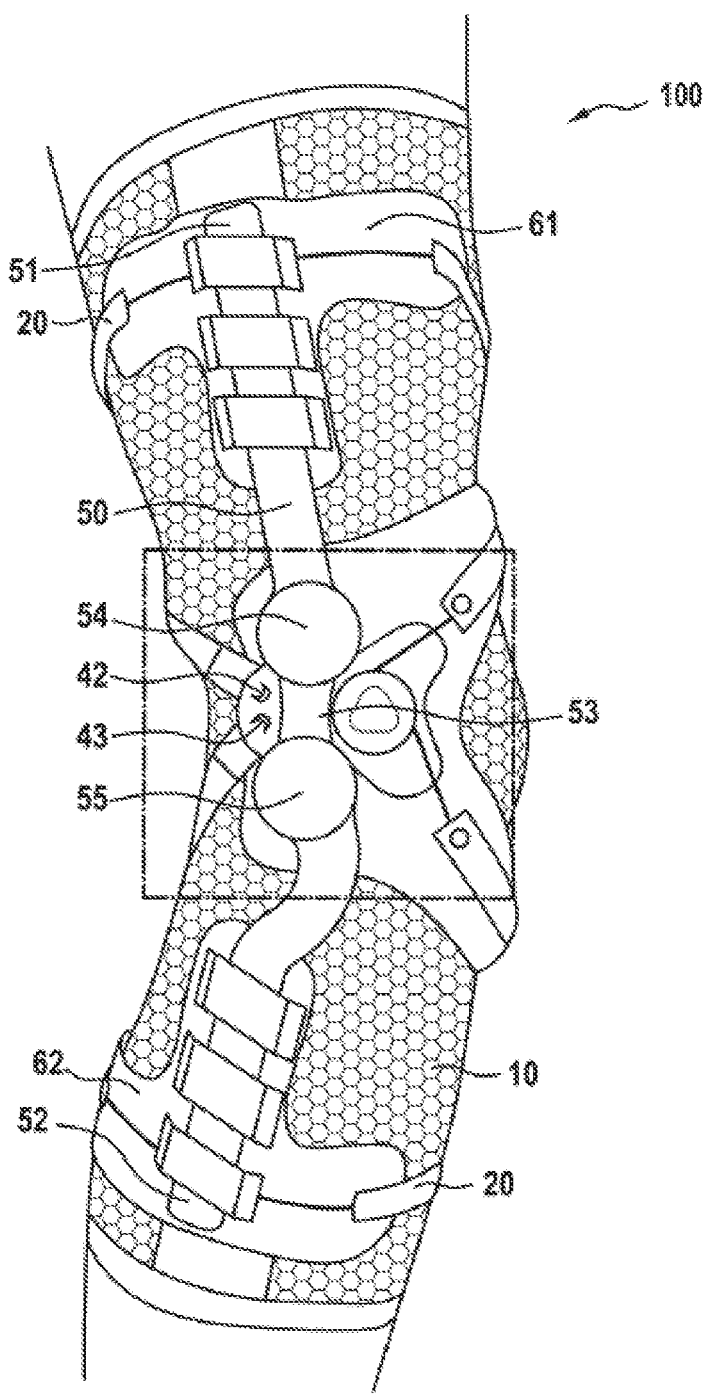
Figure 2B:
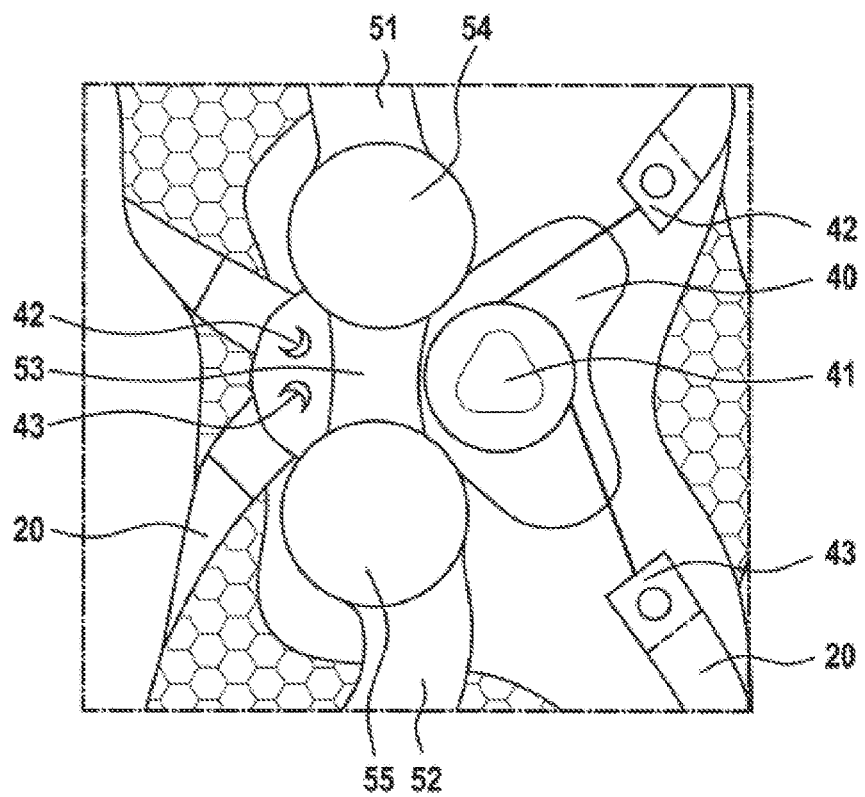
Figure 3:
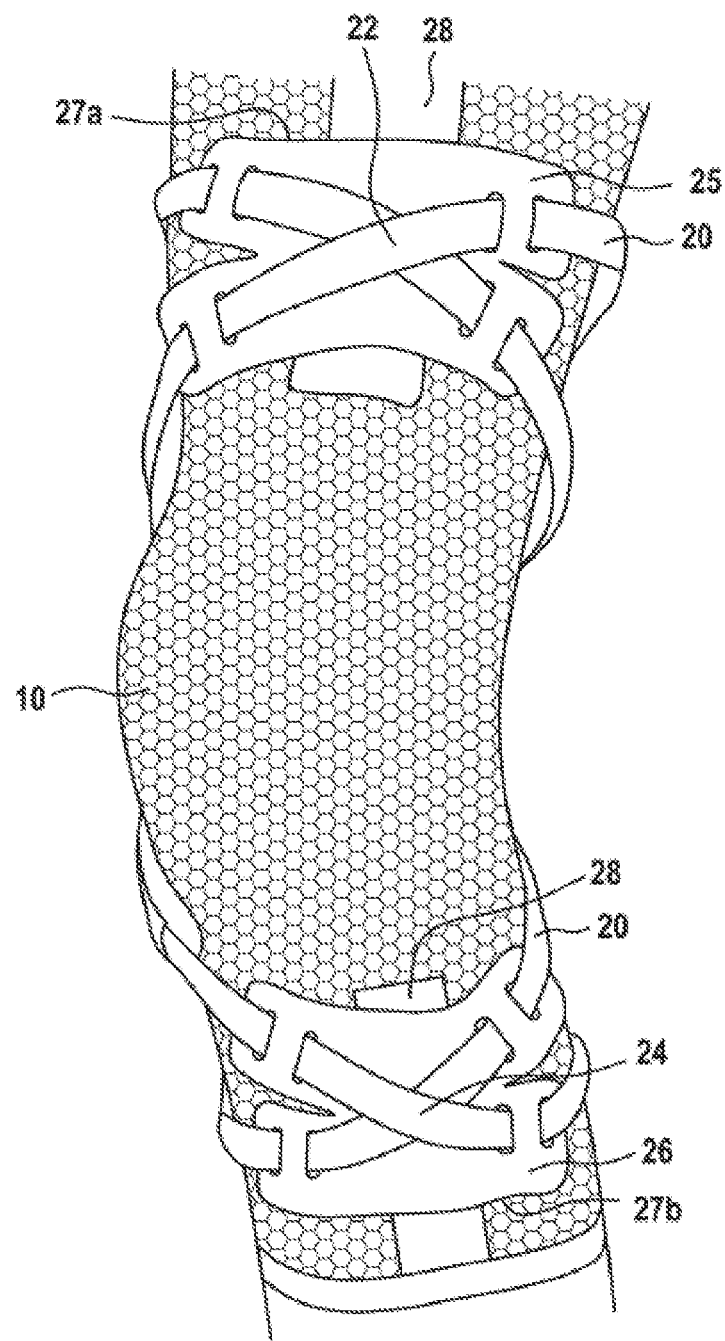
Figure 4:
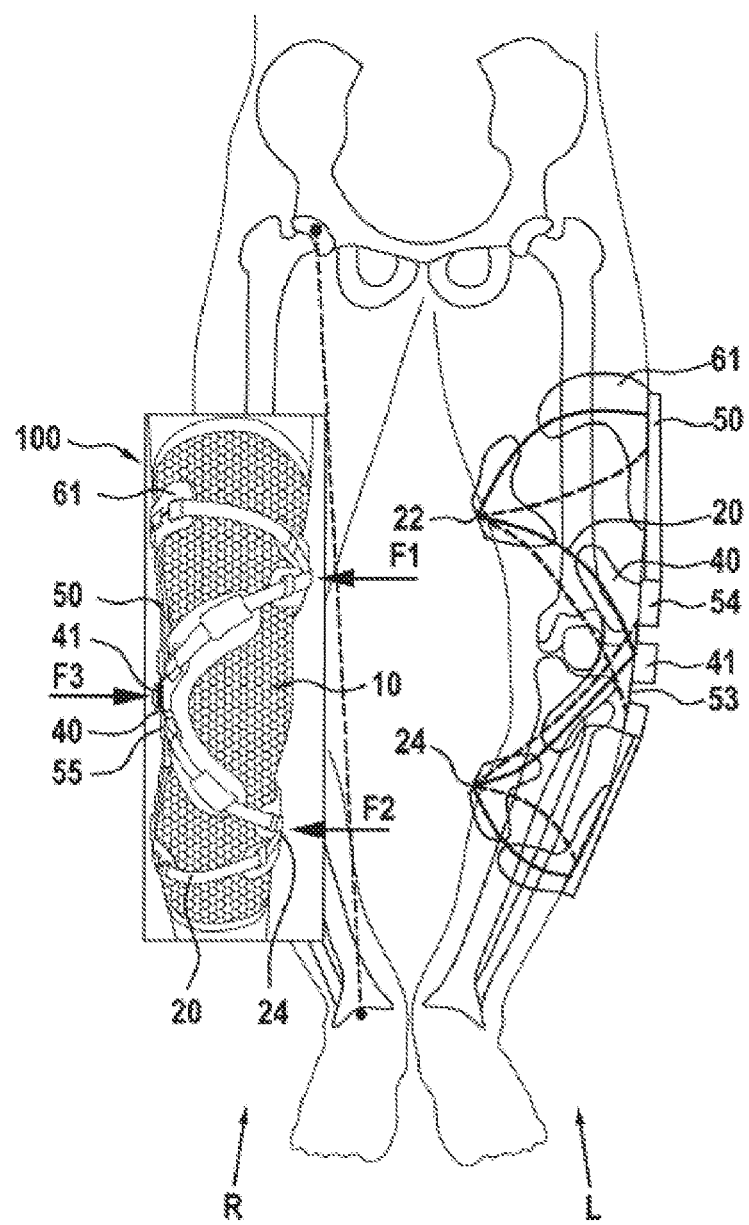
Figure 5:
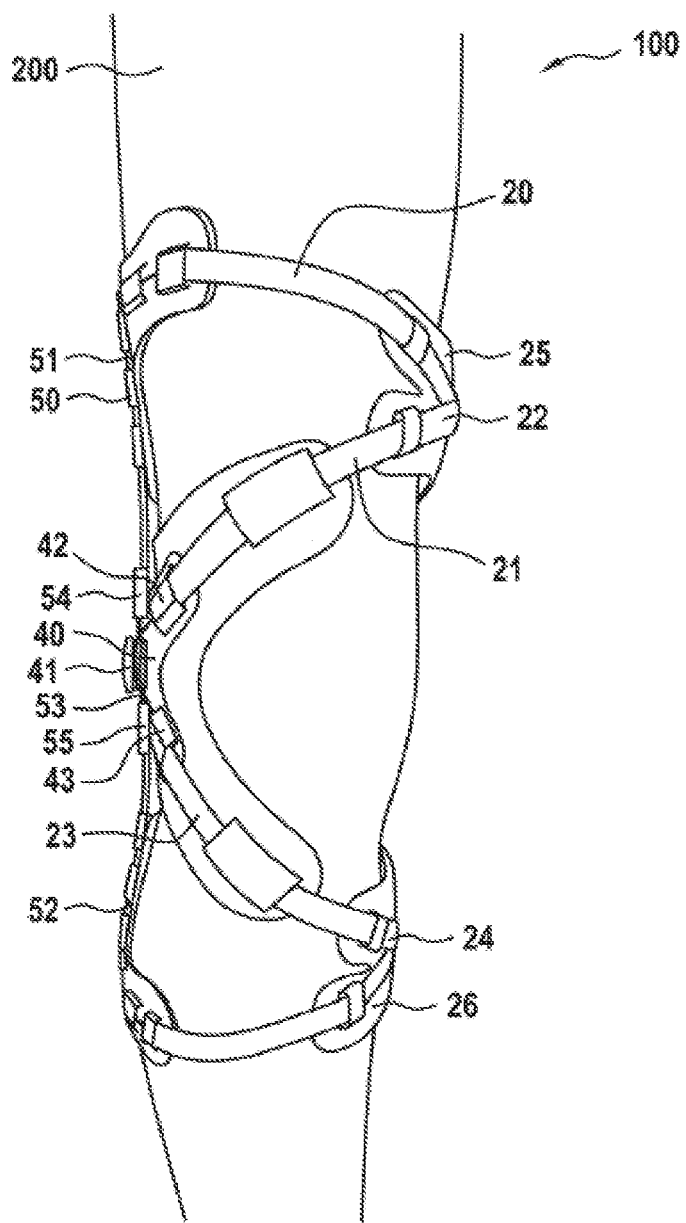
Figure 6:
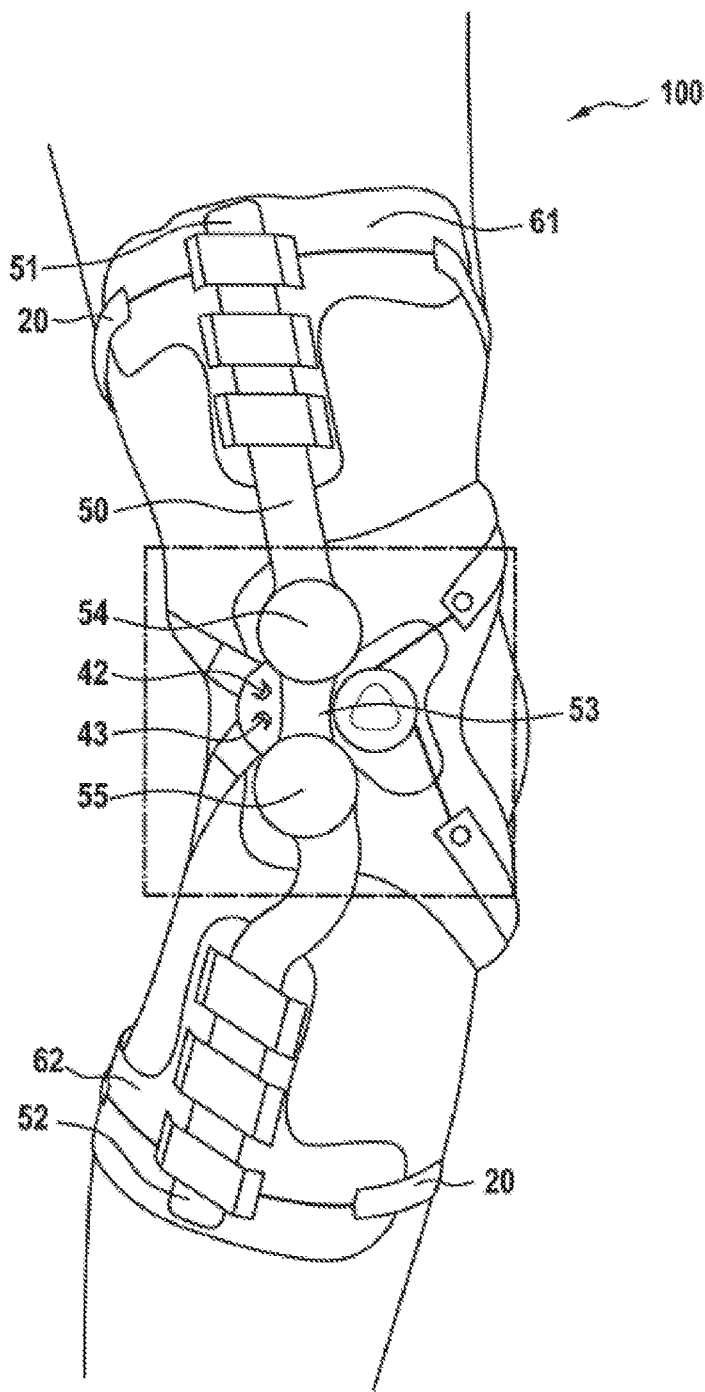
Figure 7:
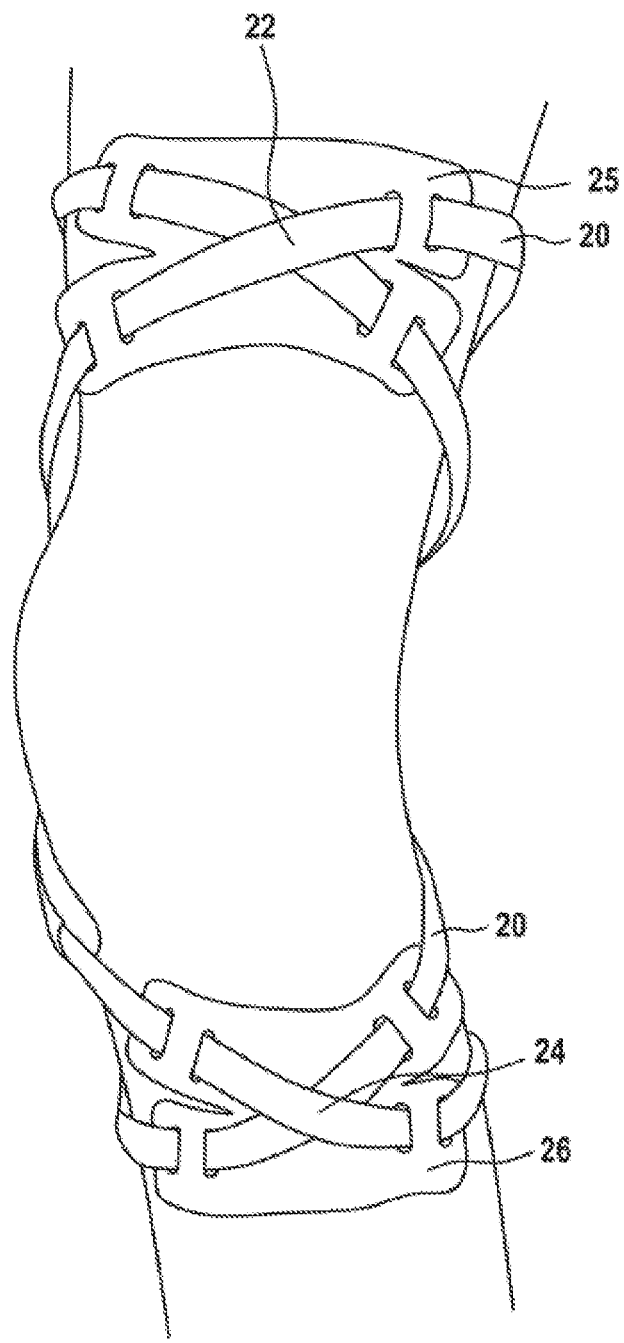
Figure 8:
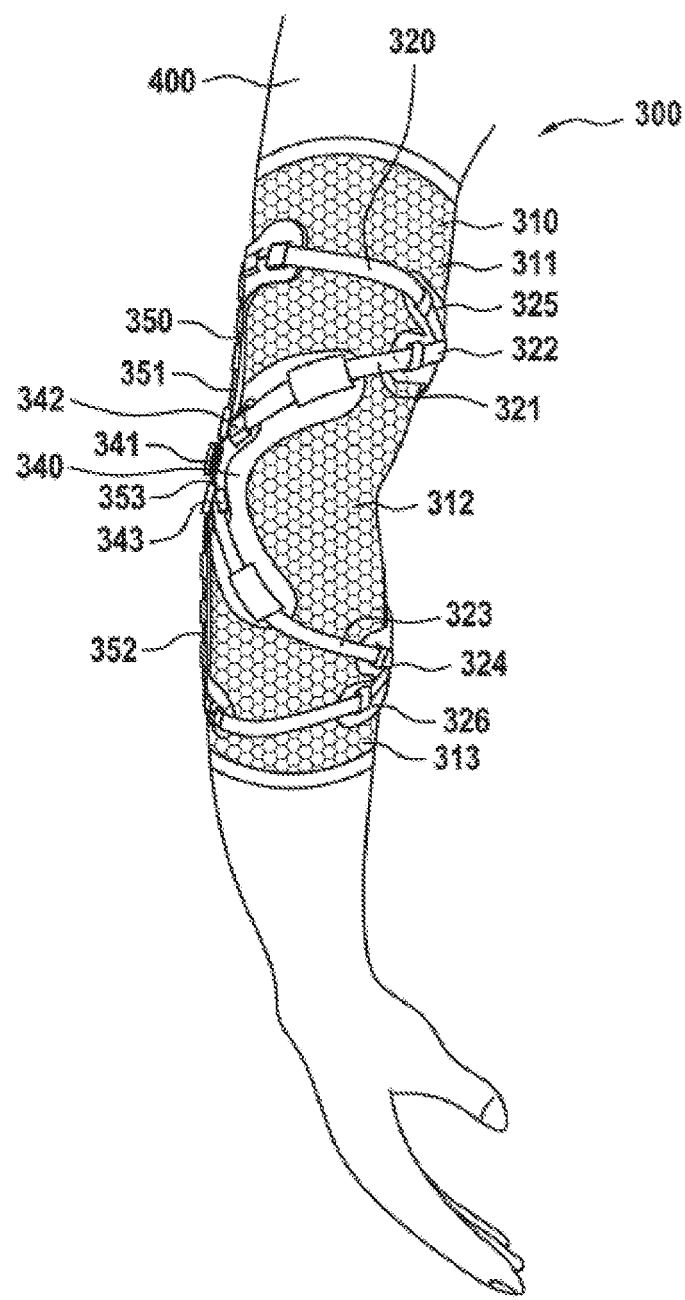
Figure 9:
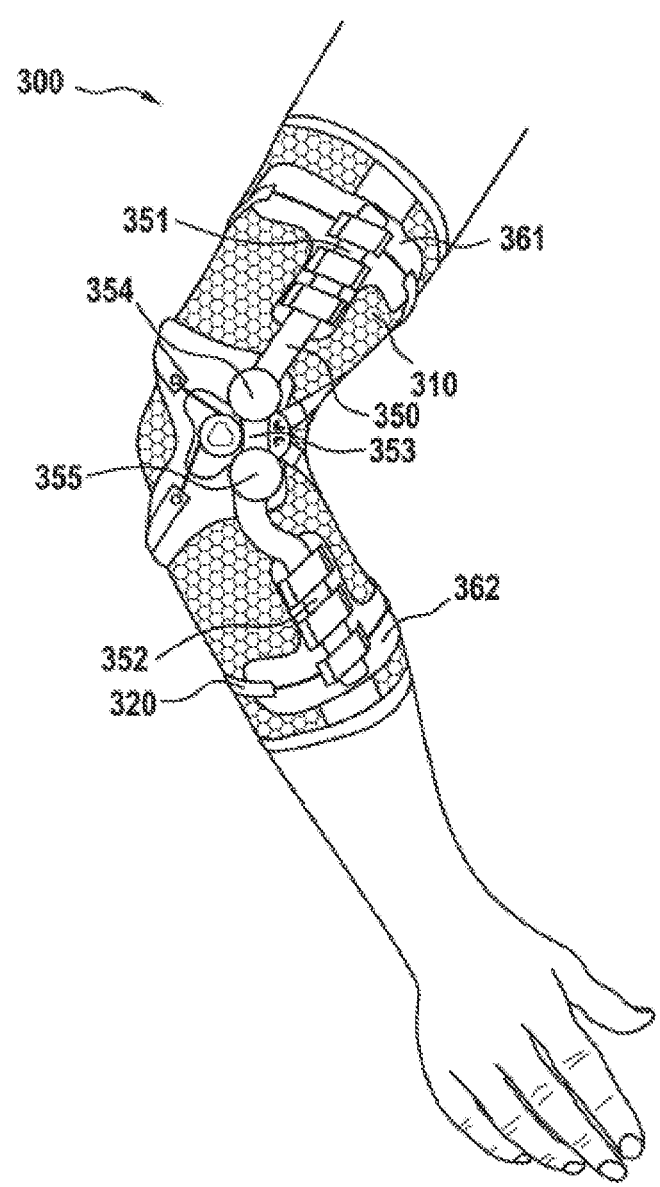
Figure 10:
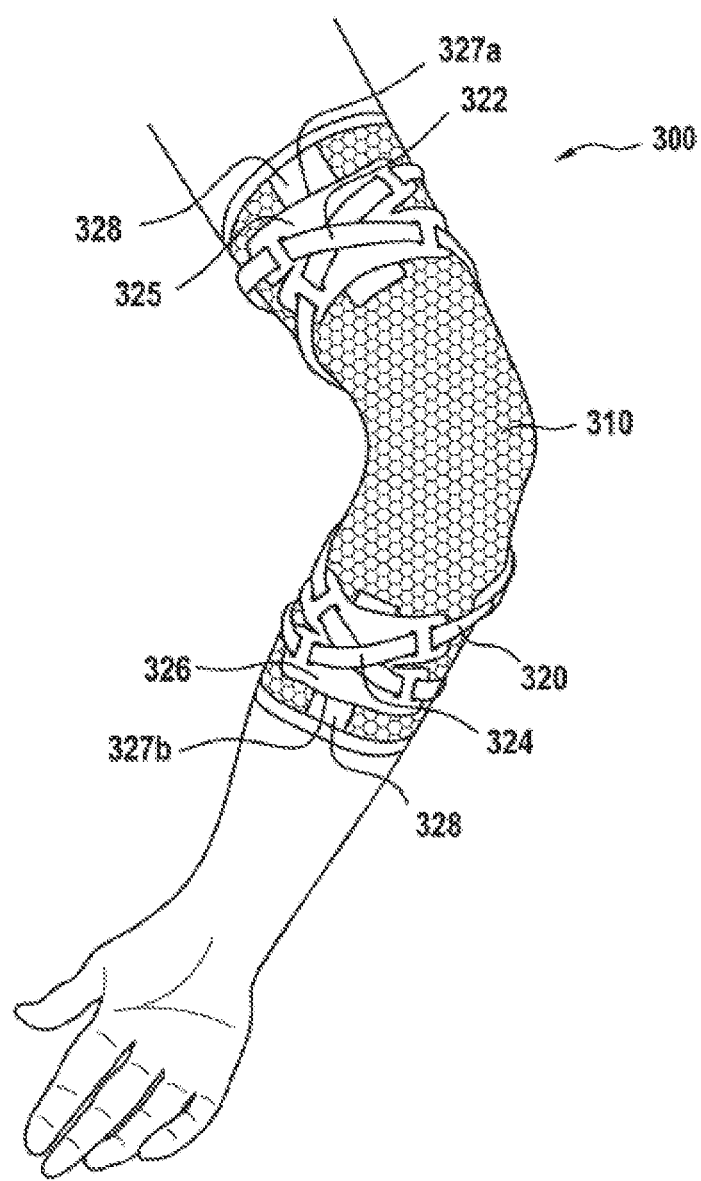
Figure 11:
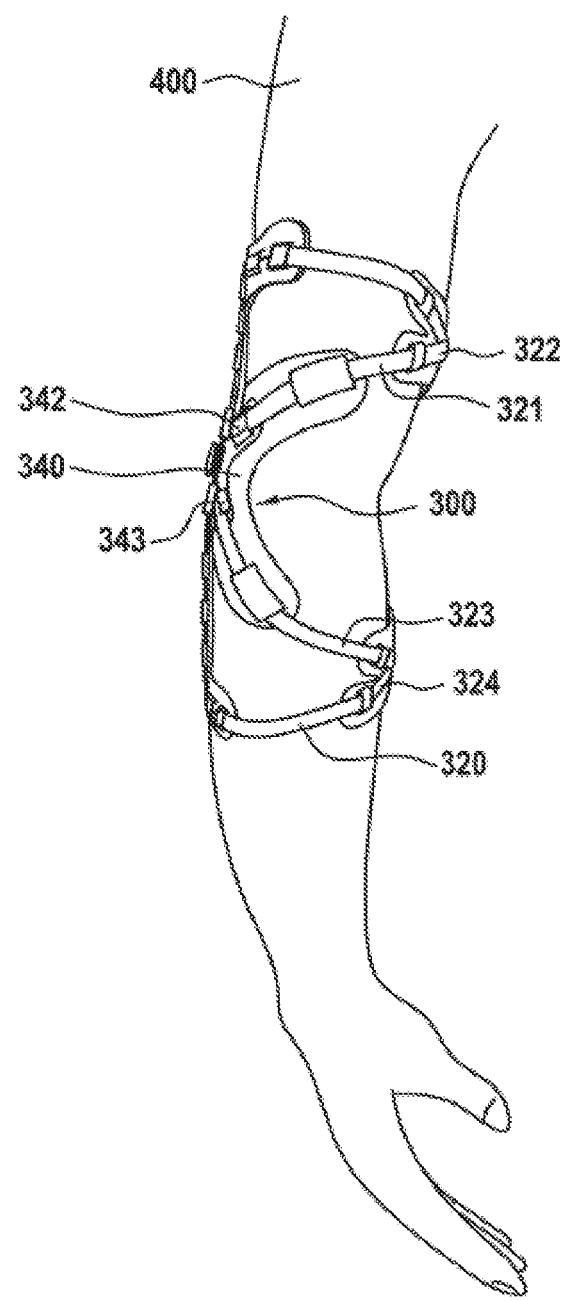
Figure 12:
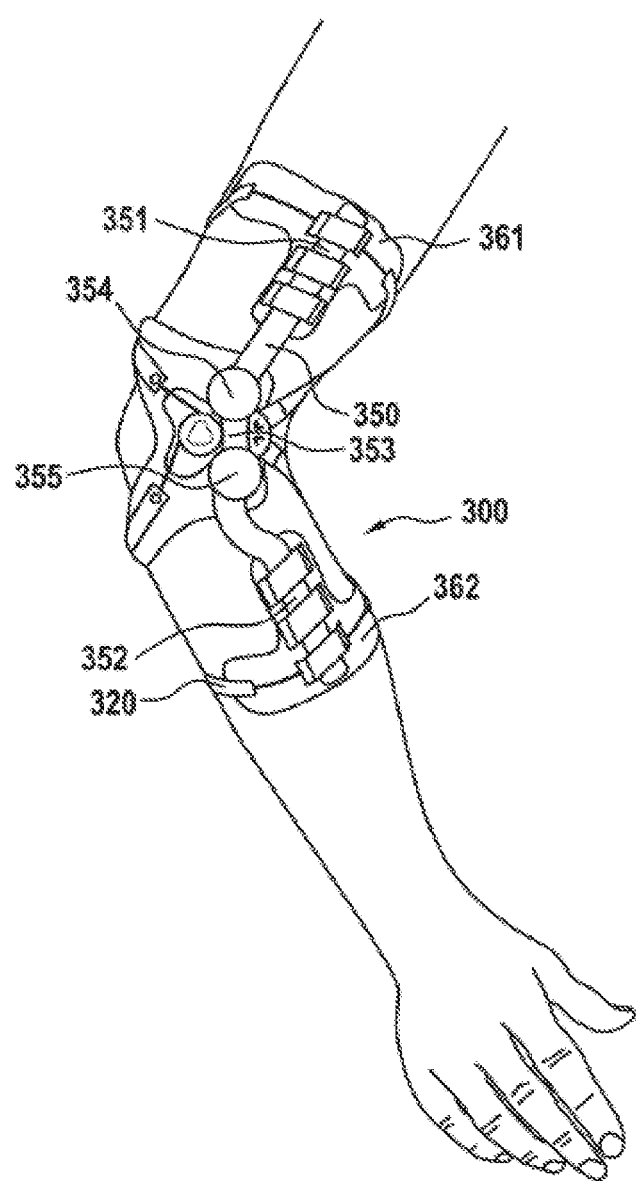
Figure 13:
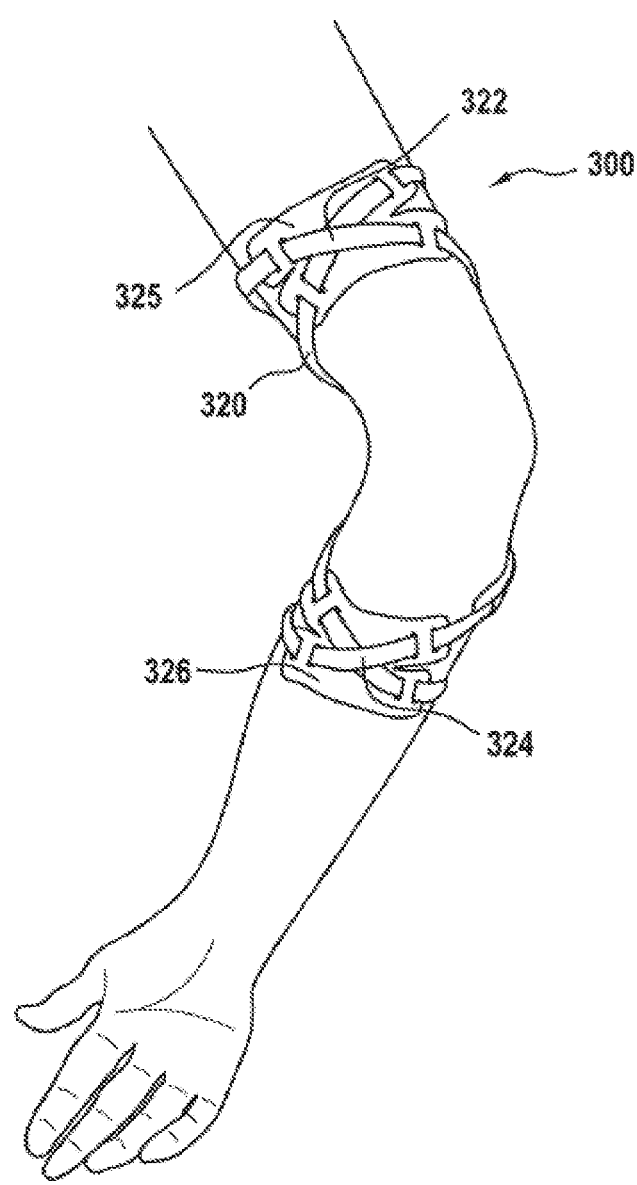

FIG. 1 depicts a knee orthosis according to the invention in a frontal view;
FIG. 2a depicts the outside of the knee orthosis of FIG. 1;
FIG. 2b depicts a detailed section of FIG. 2a;
FIG. 3 depicts the inside of the knee orthosis of FIG. 1;
FIG. 4 depicts a schematic drawing of the force effect of the knee orthosis according to the invention;
FIG. 5 depicts another knee orthosis according to the invention in a frontal view;
FIG. 6 depicts the outside of the knee orthosis of FIG. 5;
FIG. 7 depicts the inside of the knee orthosis of FIG. 5;
FIG. 8 depicts an elbow orthosis according to the invention in a frontal view;
FIG. 9 depicts the elbow orthosis of FIG. 8 when the arm is bent;
FIG. 10 depicts the inside of the elbow orthosis of FIG. 8;
FIG. 11 depicts another elbow orthosis according to the invention in a frontal view;
FIG. 12 depicts the elbow orthosis of FIG. 11 when the arm is bent;
FIG. 13 depicts the inside of the elbow orthosis of FIG. 11.

EXAMPLES

Knee Orthosis:

FIG. 1 depicts for illustrative purposes a knee orthosis (100) according to the invention in a frontal view on a leg (200), having a textile support as a carrier element (10) having an upper subregion (11), a central subregion (12) and a lower subregion (13). Coupled to the carrier element (10) via a coupling element (40) is a strap system (20), wherein a first strap as a first section (21) of the strap system (20) is routed around the upper subregion (11) of the carrier element (10) in such a manner that the strap crosses over in a first crossover region (22) and wherein a second strap as a second section (23) of the strap system (20) is routed around the lower subregion (13) of the carrier element (10) in such a manner that the strap crosses over in a second crossover region (24). Both sections (21, 23) of the strap system (20) are thereby each designed as slings, thus wrapping around the respective region of the leg (200).

The coupling element (40) is attached to the central subregion (12) on the carrier element (10) and the strap system (20) is movably attached to the coupling element (40) via suspension means (42, 43). The coupling element (40) has a rotary knob (41) as a tensioning element for tensioning the strap of the first section (21) of the strap system (20) and for simultaneously tensioning the strap of the second section (23) of the strap system (20). Tensioning occurs by winding up cables, connected to the straps, onto a spool in the rotary knob (40).

The straps (21, 23) of the strap system (20) are formed of cords that run in flat strip tunnels. In the drawings, one can see primarily these flat strip tunnels of the strap system (20) and not the tensionable cords running in them.

The strap system (20) has a first crossing element (25), in which the strap is routed in the first crossover region (22) and a second crossing element (26) in which the strap is routed in the second crossover region (24), wherein the first crossing element (25) is reversibly attached by means of a hook and loop connection (27a) to the upper subregion (11) of the carrier element (10), and that the second crossing element (26) is reversibly attached by means of a hook and loop connection (27b) to the lower subregion (13) of the carrier element (10). The crossover regions (22, 24) are positioned on the region of the support contacting the inside of the leg.

The knee orthosis (100) also has a joint splint (50), which is mounted on the support (10) in the region of the outside of the leg. The joint splint (50) has a first bar section (51) in the region of the upper subregion (11) of the carrier element (10), a second bar section (52) in the region of the lower subregion (1.3) of the carrier element (10) and a third bar section (53) in the region of the central subregion (12) of the carrier element (10). The first bar section (51) and the second bar section (52) are each connected by means of a monocentric joint (54, 55) to the third bar section (53). The third bar section (53) is designed as a spring element in the form of a leaf spring. The coupling element (40) is attached to the central subregion (12) so that the strap system (20) exerts a tensile force on this region of the joint splint (50) when tensioning the straps. The strap system (20) also secures the joint splint (50) at its upper and lower ends.

FIG. 2a depicts the outside of the knee orthosis (100) of FIG. 1. One can clearly see the support (10) with the abutting joint splint (50), which is again divided into the three subregions (51, 52, 53), and which are connected to each other by the two monocentric hinge joints (54, 55). At the top and bottom, the strap system (20) is connected to the joint splint (50) by means of plate elements (61, 62).

The straps of the strap system (20) are connected to the coupling element by means of movable suspension means (42, 43).

FIG. 2b depicts an enlarged section of the third bar section (53) from FIG. 2a. The third, central bar section is designed as a leaf spring (53) and is connected to the two other sections (51, 52) of the joint splint by means of the two hinged joints (54, 55). Located on the central bar section (53) is the coupling element (40) with the rotary knob (41) as a tensioning element. The straps of the strap system (20) are connected to the coupling element (40) via movable suspension means (42, 43).

FIG. 3 depicts the inside of the knee orthosis of FIG. 1. One can clearly see the support (10) with the crossover regions (22, 24) of the strap system (20), which are routed into the crossing elements (25, 26). The crossing elements (25, 26) are attached in a flexible and repositionable manner to loop regions (28) of the support (10) by means of underside hook connections (27a, 27b). The two crossover regions (22, 24) create a strap routing of the strap system (20) in the form of a double figure-eight.

FIG. 4 depicts a schematic drawing of the force effect of the knee orthosis (100) according to the invention on a bow-legged misalignment. On the right leg (R), one can see the knee orthosis (100) from FIG. 1; on the left leg (L), one can see a schematic drawing with key sub-elements. On both sides, one can see the strap system (20) with the crossover regions (22, 24), the coupling element (40) with the rotary knob (41) for tensioning the strap system (20), a plate element (61) and the joint splint (50) that is again divided into three subregions, which are connected to each other by means of the two monocentric hinged joints (54, 55). On the left leg (L), one can see how the center bar section (53), designed to be springy, is bent in a springy manner by the bow leg. By the doubly crossed routing of the strap system (20), the joint splint (50) is well pressed in a positionally stable manner on the outside of the leg against the carrier element (10) and thus the leg, since the two inside crossover regions (22, 24) act as outwardly acting counterforces (F1, F2) in relation to the inward acting force (F3) of the coupling element (40), which is attached to the joint splint (50). In this way, the knee orthosis (100) acts biomechanically according to the three-forces principle.

FIG. 5 depicts for illustrative purposes a knee orthosis (100) according to the invention having a strap system (20) as in FIG. 1 in a frontal view on a leg (200), yet in an embodiment without a carrier element. The strap system (20) is coupled to a coupling element (40), wherein a first strap as a first section (21) of the strap system (20) is routed in such a manner that the strap crosses over in a first crossover region (22) and wherein a second strap as a second section (23) of the strap system (20) is routed in such a manner that the strap crosses over in a second crossover region (24).

The strap system (20) is movably attached to the coupling element (40) by means of suspension means (42, 43). The coupling element (40) has a rotary knob (41) as a tensioning element for tensioning the strap of the first section (21) of the strap system (20) and for the simultaneous tensioning of the strap of the second section (23) of the strap system (20). Tensioning occurs by winding up cables connected to the straps onto a spool in the rotary knob (40). The straps (21, 23) of the strap system (20) are formed of cords, which run in flat strip tunnels. In the drawings, one can see primarily these flat strip tunnels of the strap system (20) and not the tensionable cords running in them.

The strap system (20) has a first crossing element (25) in which the strap is routed in the first crossover region (22) and a second crossing element (26) in which the strap is routed in a second crossing region (24). The crossover regions (22, 24) are positioned on the inside of the leg.

The knee orthosis (100) also has a joint splint (50), which is mounted in the region of the outside of the leg. The joint splint (50) has a first bar section (51), a second bar section (52) and a third bar section (53). The first bar section (51) and the second bar section (52) are each connected by means of a monocentric joint (54, 55) to the third bar section (53). The third bar section (53) is designed as a spring element in the form of a leaf spring. The coupling element (40) is attached to the strap system (20) and the joint splint (50) so that the strap system (20) exerts a tensile force on this region of the joint splint (50) when tensioning the straps. The strap system (20) also secures the joint splint (50) on its upper and lower ends.

FIG. 6 depicts the outside of the knee orthosis (100) of FIG. 5. One can clearly see the joint splint (50), which is again divided into three subregions (51, 52, 53) that are connected to each other by the two monocentric hinged joints (54, 55). At the top and bottom, the strap system (20) is connected to the joint splint (50) by means of plate elements (61, 62).

The straps of the strap system (20) are connected to the coupling element by means of movable suspension means (42, 43).

FIG. 7 depicts the inside of the knee orthosis of FIG. 5. One can clearly see the crossover regions (22, 24) 495 of the strap system (20), which are routed into the crossing elements (25, 26). The two crossover regions (22, 24) create a strap routing of the strap system (20) in the form of a double figure-eight.

Elbow Orthosis

FIG. 8 depicts for illustrative purposes an elbow orthosis (300) according to the invention in a frontal view on an arm (400), having a textile support as a carrier element (310) having an upper subregion (311), a central subregion (312) and a lower subregion (313). Coupled to the carrier element (310) via a coupling element (340) is a strap system (320), wherein a first strap as a first section (321) of the strap system (320) is routed around the upper subregion (311) of the carrier element (310) in such a manner that the strap crosses over in a first crossover region (322) and wherein a second strap as a second section (323) of the strap system (320) is routed around the lower subregion (313) of the carrier element (310) in such a manner that the strap crosses over in a second crossover region (324). Both sections (321, 323) of the strap system (320) are thereby each designed as slings, thus wrapping around the respective region of the arm (400).

The coupling element (340) is attached to the central subregion (312) on the carrier element (310) and the strap system (320) is movably attached to the coupling element (340) via suspension means (342, 343). The coupling element (340) has a rotary knob (341) as a tensioning element for tensioning the strap of the first section (321) of the strap system (320) and for simultaneously tensioning the strap of the second section (323) of the strap system (320). Tensioning occurs by winding up cables, connected to the straps, onto a spool in the rotary knob (340).

The straps (321, 323) of the strap system (320) are formed of cords that run in flat strip tunnels. In the drawings, one can see primarily these flat strip tunnels of the strap system (320) and not the tensionable cords running in them.

The strap system (320) has a first crossing element (325), in which the strap is routed in the first crossover region (322) and a second crossing element (326) in which the strap is routed in the second crossover region (324).

The elbow orthosis (300) also has a joint splint (350), which is mounted on the support (310) in the region of the outside of the arm. The joint splint (350) has a first bar section (51) in the region of the upper subregion (311) of the carrier element (310), a second bar section (352) in the region of the lower subregion (313) of the carrier element (310) and a third bar section (353) in the region of the central subregion (312) of the carrier element (310). The first bar section (351) and the second bar section (352) are each connected by means of a monocentric hinge to the third bar section (353). The third bar section (353) is designed as a spring element in the form of a leaf spring. The coupling element (340) is attached to the central subregion (312) so that the strap system (320) exerts a tensile force on this region of the joint splint (350) when tensioning the straps. The strap system (320) also secures the joint splint (350) at its upper and lower ends.

FIG. 9 depicts the outside of the elbow orthosis (300) of FIG. 8. One can clearly see the support (310) with the abutting joint splint (350), which is again divided into the three subregions (351, 352, 353), and which are connected to each other by the two monocentric hinge joints (354, 355). At the top and bottom, the strap system (320) is connected to the joint splint (350) by means of plate elements (361, 362).

FIG. 10 depicts the inside of the elbow orthosis (300) of FIG. 8. One can clearly see the support (310) with the crossover regions (322, 324) of the strap system (320), which are routed into the crossing elements (325, 326). The crossing elements (325, 326) are attached in a flexible and repositionable manner to the loop region (328) of the support (310) by means of underside hook connections (327a, 327b). The two crossover regions (322, 324) create a strap routing of the strap system (320) in the form of a double figure-eight.

FIG. 11 depicts for illustrative purposes an elbow orthosis (300) according to the invention having a strap system (320) as in FIG. 8 in a frontal view on an arm (400), yet in an embodiment without a carrier element. The strap system (320) is coupled to a coupling element (340), wherein a first strap as a first section (321) of the strap system (320) is routed in such a manner that the strap crosses over in a first crossover region (322) and wherein a second strap as a second section (323) of the strap system (320) is 555 routed in such a manner that the strap crosses over in a second crossover region (324), The strap system (320) is movably attached to the coupling element (340) by means of suspension means (342, 343). In regard to the further construction of the orthosis (300), one shall refer to the description of FIGS. 5 and 8.

FIG. 12 depicts the outside of the elbow orthosis (300) of FIG. 11. One can clearly see the joint splint (350), which is again divided into the three subregions (351, 352, 353), and which are connected to each other by the two monocentric hinge joints (354, 355). At the top and bottom, the strap system (320) is connected to the joint splint (350) by means of plate elements (361, 362).

FIG. 13 depicts the inside of the elbow orthosis (300) of FIG. 11. One can clearly see the crossover regions (322, 324) of the strap system (320), which are routed into the crossing elements (325, 326). The two crossover regions (322, 324) create a strap routing of the strap system (320) in the form of a double figure-eight.

The invention claimed is:

1. A limb orthosis comprising:
a first strap comprising a first end and a second end, and configured to wrap around an upper limb, being routed at least once entirely around the upper limb, and cross over itself at least once at a first cross over region at the upper limb when the limb orthosis is in a donned state;
a second strap comprising a first and a second end, and configured to wrap around a lower limb, being routed at least once entirely around the lower limb, and cross over itself at least once at a second cross over region at the lower limb when the limb orthosis is in the donned state; and
a coupling element comprising a tensioning element, the coupling element configured to contact the limb at a level of a knee or an elbow when the limb orthosis is in the donned state,
wherein the first end of the first strap and the first end of the second strap is attached to the coupling element,
wherein the second end of the first strap and the second end of the second strap is connected to the tensioning element, and the tensioning element is configured ot simultaneously tension the first strap and the second strap.

2. The limb orthosis according to claim 1, further comprising a carrier element having an upper sub-region, a central sub-region and a lower sub-region, wherein the first and second straps are coupled to the carrier element by means of the coupling element, wherein the first strap is routed around the upper sub-region of the carrier element in such a manner that the first strap crosses over at the first crossover region and that the second strap is routed around the lower sub-region of the carrier element in such a manner that the second strap crosses over at the second crossover region.

3. The limb orthosis according to claim 2, wherein the limb orthosis has a joint splint.

4. The limb orthosis according to claim 3, wherein the joint splint has a first bar section, a second bar section and a third bar section, and wherein the first bar section and the second bar section are each connected by a joint to the third bar section.

5. The limb orthosis according to claim 4, wherein the third bar section is formed of a spring element.

6. The limb orthosis according to claim 3, wherein the joint splint has a first bar section extending over the upper sub-region of the carrier element, a second bar section extending over the lower sub-region of the carrier element and a third bar section extending over the central sub-region of the carrier element , and wherein the first bar section and the second bar section are each connected by a joint to the third bar section.

7. The limb orthosis according to claim 2, wherein the carrier element is a support.

8. The limb orthosis according to claim 2, wherein the coupling element is attached to the central sub-region on the carrier element.

9. The limb orthosis according to claim 2, further comprising first crossing element in which the first strap is routed in the first crossover region and has-a second crossing element in which the second strap is routed in the second crossover region, wherein the first crossing element is configured to be attached to the upper sub-region of the carrier element and the second crossing element is configured to be attached to the lower sub-region of the carrier element.

10. The limb orthosis according to claim 1, wherein the limb is a leg.

11. The limb orthosis according to claim 1, wherein the coupling element is configured to be positioned on an outer side of the limb when the limb orthosis is in the donned state.

12. The limb orthosis according to claim 1, wherein the limb orthosis is a knee orthosis.

13. The limb orthosis according to claim 1, wherein the first and second straps are movably attached to the coupling element.

14. The limb orthosis according to claim 1, wherein the first and second straps are two separate straps.

* * * * *